US 6,698,429 B2

(12) United States Patent
Croll et al.

(10) Patent No.: US 6,698,429 B2
(45) Date of Patent: Mar. 2, 2004

(54) MEDICAL ATOMIZER

(75) Inventors: Perry W. Croll, Salt Lake City, UT (US); Marshall T. Denton, Salt Lake City, UT (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 104 days.

(21) Appl. No.: 10/099,486

(22) Filed: Mar. 15, 2002

(65) Prior Publication Data

US 2003/0172934 A1 Sep. 18, 2003

(51) Int. Cl.[7] ............................................. A61M 16/00
(52) U.S. Cl. ............................ 128/207.14; 128/200.14
(58) Field of Search ................. 128/200.24, 200.11, 128/200.13, 200.14, 200.18, 200.21, 200.22, 203.12, 203.23, 207.14, 207.15; 239/482, 483, 490, 491

(56) References Cited

U.S. PATENT DOCUMENTS

| | | | | |
|---|---|---|---|---|
| 5,031,613 A | * | 7/1991 | Smith et al. | 128/207.14 |
| D333,000 S | | 2/1993 | Good et al. | |
| 5,233,979 A | * | 8/1993 | Strickland | 128/207.14 |
| 5,246,012 A | * | 9/1993 | Strickland | 600/581 |
| D340,185 S | | 10/1993 | Martone | |
| D344,231 S | | 2/1994 | Gagnon | |
| 5,284,132 A | * | 2/1994 | Geier | 128/200.22 |
| 5,291,882 A | * | 3/1994 | Makhoul et al. | 128/207.14 |
| 5,490,630 A | | 2/1996 | Hecker | |
| 5,511,538 A | | 4/1996 | Haber et al. | |
| 5,601,077 A | | 2/1997 | Imbert | |
| 5,803,078 A | * | 9/1998 | Brauner | 128/207.14 |
| 5,964,223 A | * | 10/1999 | Baran | 128/207.14 |
| 5,971,357 A | * | 10/1999 | Denton et al. | 251/144 |
| 6,009,868 A | * | 1/2000 | Nilson | 128/200.18 |
| 6,079,413 A | * | 6/2000 | Baran | 128/207.14 |
| 6,112,743 A | | 9/2000 | Denton | |
| 6,526,976 B1 | * | 3/2003 | Baran | 128/207.14 |
| 6,543,703 B2 | * | 4/2003 | Blake | 239/106 |
| 6,575,944 B1 | * | 6/2003 | McNary et al. | 604/264 |

OTHER PUBLICATIONS

Official Gazette, p. 2224, Apr. 15, 1997.
"Meeting the Challenge . . . ", *Valois Pharm.*, pp. 1–12.

* cited by examiner

*Primary Examiner*—Aaron J. Lewis
*Assistant Examiner*—Teena Mitchell
(74) *Attorney, Agent, or Firm*—TraskBritt

(57) ABSTRACT

An atomizing nozzle which may be embodied having particular utility to dispense fluid as a mist at an exit of an endotracheal tube. The nozzle may be adapted to maintain a dry exit surface, and to resist unintended leakage of a medication. In one embodiment, a pressure of about 5 psi is required to initiate a discharge of fluid from the nozzle exit orifice.

29 Claims, 6 Drawing Sheets

MEDICAL ATOMIZER

TECHNICAL FIELD

The invention relates to atomizing nozzles and devices which dispense fluids in a misted or dispersed, small particle size, form. Certain devices constructed according to the instant invention are particularly suitable for use in pulmonary therapy. The invention also relates to atomizers having a one-way valve to resist leakage of pre-loaded fluids and nozzle dribble subsequent to a fluid discharge.

BACKGROUND

Atomizing nozzles are used for delivery of fluids, including medications, in a dispersed, or misted, form to both external and internal surface areas of a subject. A range of typical commercially available atomizing nozzles and atomizer assemblies are manufactured by Valois S.A., a French Company having a head office located at Rue Du Doyen, Jussiaume, 27110 Le Neubourg France.

Available atomizing nozzle assemblies typically have an atomizer nozzle attached to an elongate member to dispense the atomized fluid at a distance from a pressurized fluid source. A pressurizable source of medication or other fluids is either affixed or attachable to an opposite end of the elongate member. Many atomizer nozzles are sized to resist insertion of a nozzle tip too far into an orifice, such as a nostril. In use of such atomizer assemblies in pulmonary therapy, the nozzle tip may be inserted into an endotracheal tube, and the medication dispensed. Even presupposing that the nozzle itself fits within the endotracheal tube, the length of the elongate member of commercially available atomizer assemblies is less than the length of typical endotracheal tubes. Therefore, the atomized fluid unavoidably is dispensed into contact with the interior of the endotracheal tube. Droplets form on the tube wall and drip into the bronchial area of a subject, causing a gag reflex which may cause the subject to expel an indeterminate quantity of the medication though the endotracheal tube. In such case, the endotracheal tube effectively becomes a discharge nozzle, potentially dowsing medical personnel with disease bearing medication and body fluids. Besides a gag incident being uncomfortable to the subject, medical personnel are placed at risk of infection. Furthermore, the medication dose received by a subject is unreliable subsequent to a gag incident, potentially contributing to either an over- or under-medicated state in the subject.

Syringes are relatively inexpensive and capable of generating high pressures on selectable volumes of medication fluids. A syringe may be pre-filled with a desired medication dose, and attached to an atomizing nozzle. Subsequent to such attachment, it is desirable that the medication fluid not leak out of the nozzle orifice during storage prior to being dispensed. Prevention of such fluid leakage helps to maintain a sterile field about a subject. Puddles of medication fluid that has leaked from an atomizer may undesirably contaminate other instruments. Furthermore, a leaking atomizer may contain an unknown dose amount, or an undesirably small dose amount, when the medication fluid finally is dispensed.

U.S. Pat. No. 5,601,077 to Imbert discloses a one-way valve to resist leaking from a loaded syringe attached to an atomizer nozzle. The valve member is a piston-like element slidably disposed in a bore and having a wiping lip arranged as a cylindrical skirt to seal against the bore wall. The seal is adapted to deflect radially to permit fluid flow in one direction. The radial motion required by such a valve member essentially limits the extent to which a diameter of the valve may be reduced. Imbert's teachings are directed to large diameter atomizers used for nasal treatment, and as such, are not well suited to application for pulmonary therapy. In application of Imbert's devices to pulmonary therapy, an undesirably large amount of atomized fluid inherently would be deposited onto the bore of an endotracheal tube, with the resulting drops of medication contributing to causing a gag reflex in a subject. Improvements to atomizers such as Imbert's device are desired to form a device compatible with insertion into an endotracheal tube, to reduce complexity in constituent element conformation, and to provide additional dribble control.

It is desirable for an atomizer nozzle to provide a clean and dry exterior surface at its discharge end subsequent to dispensing a quantity of a medication fluid. Commercially available atomizer nozzles commonly leave a partial drop at the nozzle discharge orifice which may subsequently dribble from the orifice and undesirably wet the nozzle exterior. A protruding partial drop or a wetted nozzle exterior may undesirably transfer medication to unintended locations, including to medical personnel. The elimination of such a dribble phenomena would be an improvement to medical atomizers.

SUMMARY OF THE INVENTION

The invention may be embodied as an improved atomizer assembly for delivery of fluids, substantially as a mist, to an area. A preferred embodiment delivers atomized medications to a pulmonary area of a subject. Such a pulmonary atomizer assembly may include an atomizing nozzle having a body with a diameter sized to fit within an endotracheal tube, and a tip with a discharge orifice. The nozzle body is typically attached to a first end of an elongate tubular member, which carries a second conduit for delivery of fluids from a pressurizable fluid source. Connection structure affixed at a second end of the tubular member is generally adapted to connect the pressurizable source of fluids into fluid communication with the nozzle discharge orifice. Elongate members used in pulmonary atomizer assemblies desirably have a length sufficient to enable extending the nozzle tip to a distal position for discharge of fluids external to the endotracheal tube to reduce droplet formation on the endotracheal tube walls. Droplets formed on the endotracheal tube may drip into the bronchial area, and cause a gag reflex in a treated subject.

One preferred pulmonary atomizer has an elongate member with a length longer than about 14 inches. A suitable elongate member may be made from medical grade tubing having a diameter of about ⅛ inches. Sometimes an elongate member includes a plurality of internal conduits. In such case, a malleable wire disposed in one of the conduits can function deformably to hold a shape in the elongate member. Indicia visible on the elongate member can assist to indicate the relative position of the nozzle with respect to a distal end of an endotracheal tube installed in a subject.

The pulmonary atomizer assembly can include a branched adapter structured and arranged at a stem opening for connection to a proximal end of an endotracheal tube. The elongate member is desirably slidably extendable through a first branch opening in the branched adapter. A pulmonary assembly may also include a cap disposed at an opening of the branch housing the elongate member. In such a case, the cap can provide a wiping seal to a surface of the elongate member.

A first type of desirable atomizer nozzle for use in the pulmonary atomizer assembly has a nozzle body shaped somewhat like a thimble. The thimble provides structure at a distal interior end which defines a forward portion of a swirling chamber having inlet ports and an exit orifice. A rear portion of the swirling chamber is defined by a wetted portion of the distal end of a plug. The plug may also serve as a one-way valve member. The plug is typically deformed under an assembled self-bias such that a proximal end of the plug occludes an inlet at a distal end of the elongate member and thereby resists inadvertent discharge of a fluid from the fluid source. Deliberate pressurization of the fluid, above a certain threshold value, causes the plug to deflect sufficiently to permit discharge of fluid through the atomizer nozzle. Such a valve may permit storage of pre-loaded medications in a device without risk of medications leaking through the nozzle. In one embodiment, a threshold pressure is about 5 psi. A proximal end of the nozzle body is typically constructed and arranged for connection to the end of the elongate member.

The one-way valve can function to resist nozzle dribble. Nozzle dribble may be defined as a remnant drop, or partial drop, remaining at the distal end of an atomizing nozzle subsequent to operation of the atomizer. In such a case, the drop may flow and wet the nozzle tip, or simply protrude from the nozzle body. In either case, the exposed fluid may potentially be transferred inadvertently to undesired locations. Recall that the plug is received within a bore in the nozzle body. The plug assumes a first deformed configuration during assembly of a nozzle body to an elongate member; assumes a second deformed configuration when fluid is forced under pressure past the plug for discharge through an exit orifice; and returns to the first deformed configuration when pressure is sufficiently reduced on the fluid. Movement of the plug from the second to the first deformed configuration can retract fluid at the exit orifice back into the interior of the nozzle, whereby to help maintain a dry nozzle tip exterior. Alternatively, momentum of the fluid adjacent the nozzle distal tip can help to evacuate the distal portion of a plug chamber subsequent to the valve closing.

A second type of desirable atomizer nozzle for use in the pulmonary atomizer assembly has a tip member with at least one standoff and a surface defining a forward portion of a swirling chamber having at least one turbine port and an exit orifice. The second nozzle further typically includes a one-piece body forming a conduit for fluid communication between distal and proximal body ends. The distal end houses a post having a distal post surface configured to contact the standoff(s). A wetted portion of the post end surface also defines a rear of the swirling chamber. The second nozzle may include a plurality of standoffs, with the standoffs functioning to space apart a plurality of turbine ports. One exemplary embodiment of this type has three standoffs spacing apart 3 turbine ports.

Both types of nozzle assemblies may benefit from a fluid ring being disposed upstream of the turbine inlet ports to promote uniform fluid flow into the turbine ports. Additionally, both types of atomizer nozzles can be used in non-pulmonary therapy environments. One use for embodiments having a one-way check valve may be as atomizer assemblies which can be stored pre-loaded with vaccines for nasal treatments.

BRIEF DESCRIPTION OF THE SEVERAL VIEWS OF THE DRAWINGS

In the drawings, which illustrate what are currently considered to be the best modes for carrying out the invention.

DETAILED DESCRIPTION OF THE INVENTION

Reference will now be made to the drawings in which the various elements of the invention will be given numerical designations and in which the invention will be discussed so as to enable one skilled in the art to make and use the invention. It is to be understood that the following description is only exemplary of the principles of the present invention, and should not be viewed as narrowing the claims which follow.

Figures 1, 2:
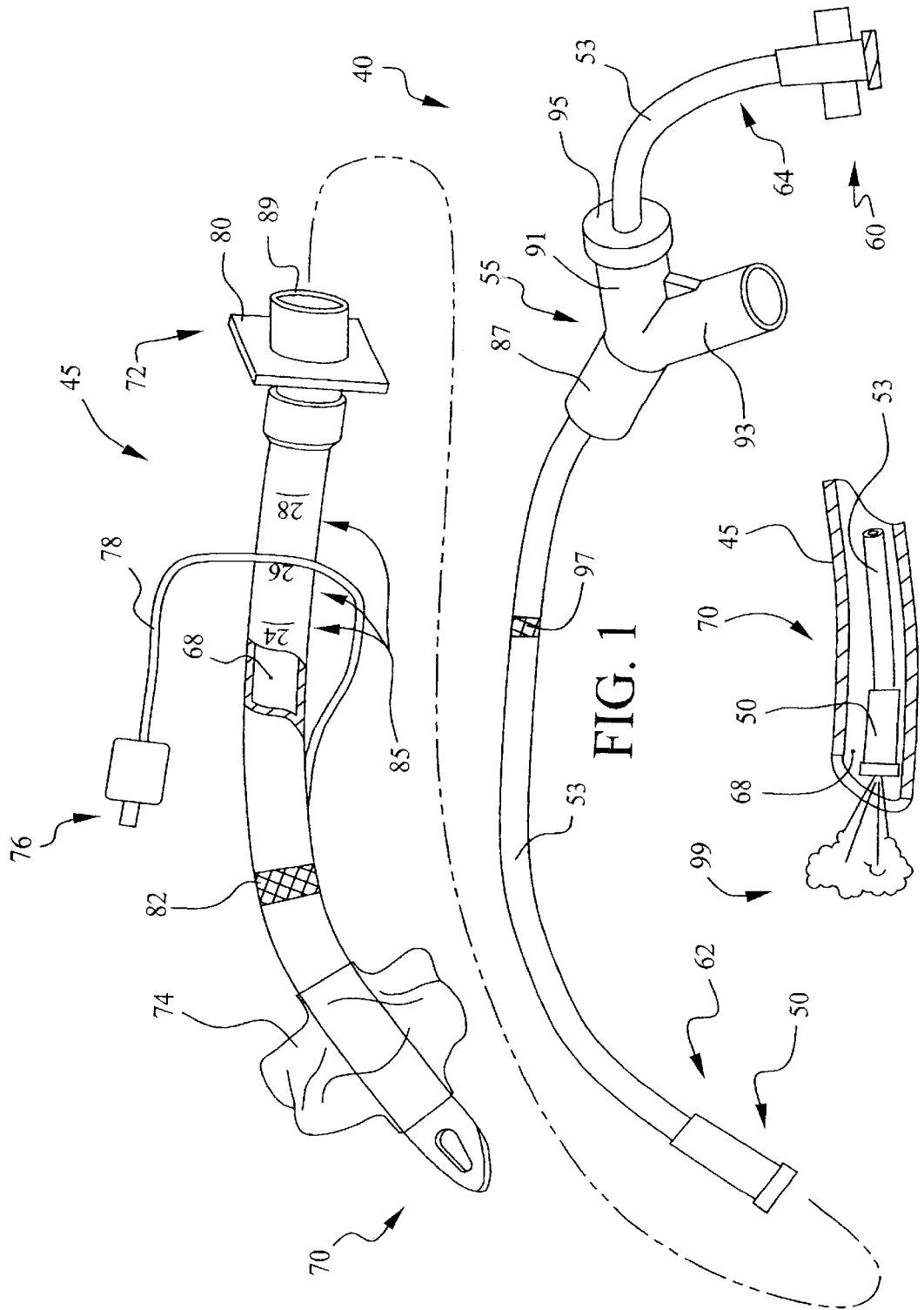
FIG. 1 is a plan view in perspective, partially in section, of an atomizer assembly configured for use with an endotracheal tube.
FIG. 2 is a perspective view of an end portion of the endotracheal tube of FIG. 1, with a nozzle tip in position to dispense treatment fluids.
Figure 3:
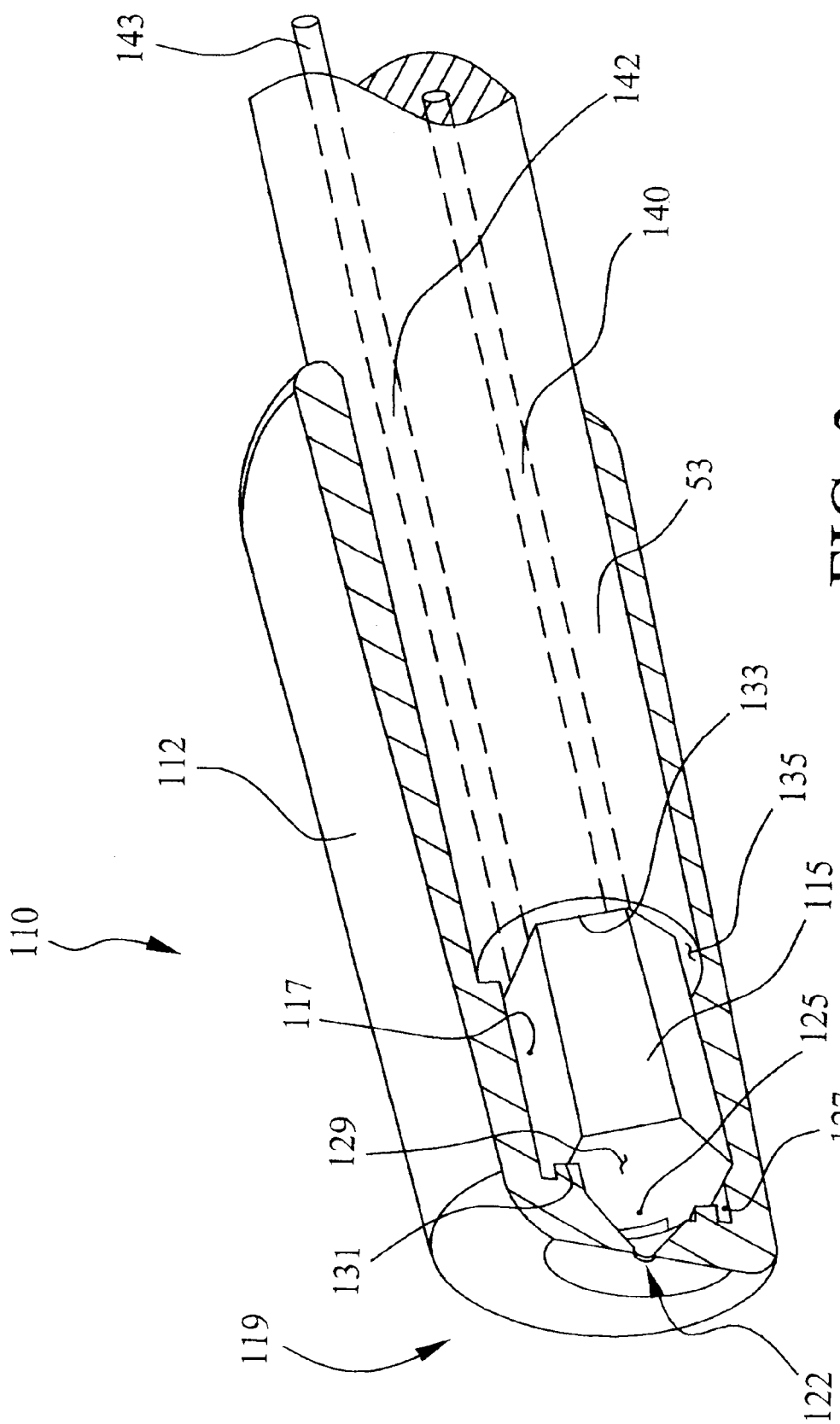
FIG. 3A is a side view in section of an atomizer nozzle with a plug installed in an uncompressed position.
FIG. 3B is a side view in section of the atomizer nozzle illustrated in FIG. 3A, but with the plug in a first compressed assembled position.
FIG. 3C is a side view in section of the atomizer nozzle illustrated in FIG. 3A, but with the plug in a second position further compressed by fluid flow.
Figure 3A:
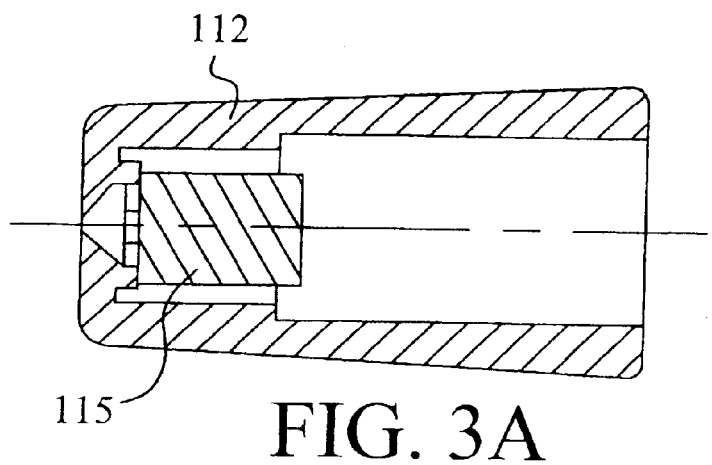
Figure 3B:
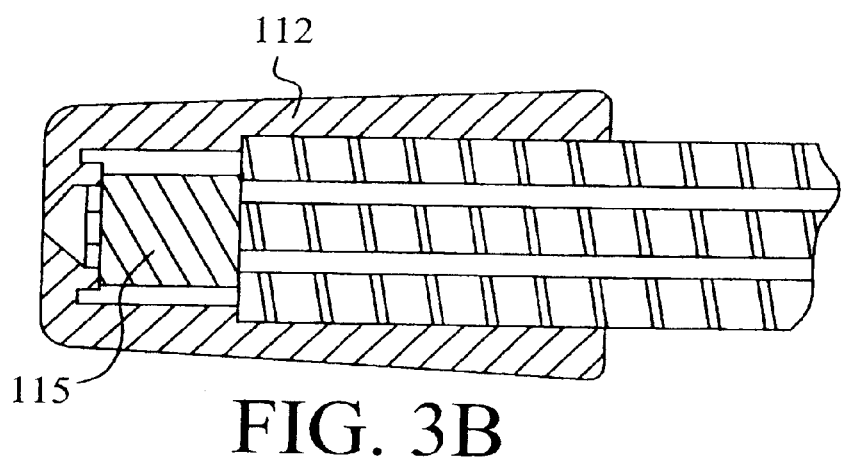
Figure 3C:
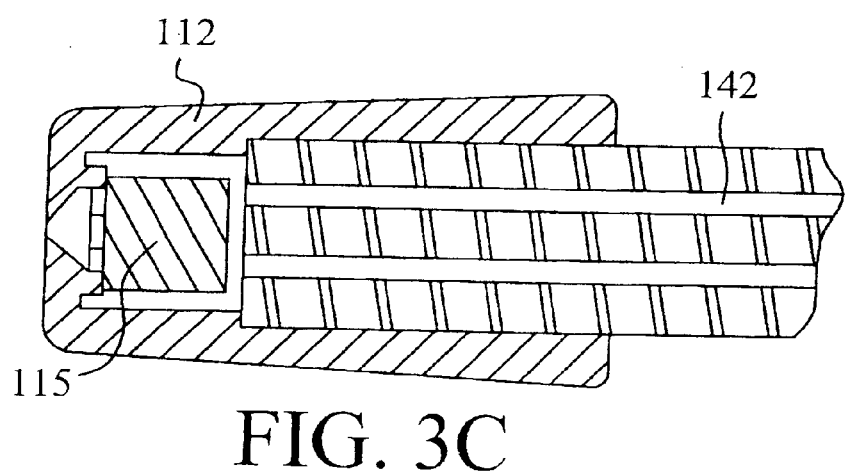

A pulmonary atomizer assembly, generally indicated at 40 and constructed according to principals of the invention, is illustrated in FIG. 1 in association with a commercially available endotracheal tube, generally indicated at 45. The assembly 40 is particularly useful to dispense medication fluids such as 2% or 4% lidocaine or verced solutions during pulmonary therapy. Other compounds for mist application are known to those of skill in the medical arts.

Pulmonary atomizer assembly 40 typically includes some sort of fluid atomizing nozzle, generally indicated at 50, an elongate tubular member 53, a branched adapter 55, and connection structure, generally indicated at 60. The nozzle 50 is affixed at a distal end, generally indicated at 62, of elongate member 53. The attach structure 60 is affixed at a proximal end, generally indicated at 64, of elongate member 53, and is adapted to connect a source of pressurizable fluid into fluid communication with a conduit through the elongate member 53. The illustrated connection structure is a LUER-lock type connector, although any structure functioning to make a fluid connection with a pressurizable source of fluids is workable.

The commercially available, generally transparent, endotracheal tube 45 includes a conduit 68 between distal and proximal ends, generally indicated at 70 and 72, respectively. A representative endotracheal tube may have a length, between its distal and proximal ends, of about 14 inches. An inflatable cuff 74 is disposed near the distal end 70, and can be inflated to seal an endotracheal tube 45 to, and hold it in a fixed position in, the throat of a subject. An inflation valve 76 is disposed in fluid communication with cuff 74 by air conduit 78 to permit inflation, and subsequently to maintain the inflation, of cuff 74. An end fitting 80 is located at proximal end 72 and serves as an insertion port or connection device for various medical apparatus. One such medical apparatus is an air bag (not shown) to assist the subject in breathing. Indicia 82 may be provided to assist in determining the extent of insertion of the tube 45 into a subject's throat. Other indicia, generally indicated at 85, may be provided as an assist to determine insertion depth of medical instrumentation, or the like, into the tube 45.

The atomizer assembly 40 may be attached to a tube 45 by feeding distal end 62 into end fitting 80 until stem member 87 can seat onto a proximal end 89 of fitting 80. Alternatively, elongate member 53 may be retracted, from the illustrated position, to bring nozzle 50 closer to adapter 55, or even substantially into stem 87 or branch 91 to facilitate connection of stem 87 to end fitting 80 of a tube 45. With the nozzle 50 located in branch 91, unimpeded access is permitted through branch 93 for insertion of medical tools, or for breathing. Additional branches may be provided in a branched adapter 55 to provide additional access locations. It is currently preferred to provide a cap 95 on a proximal end of branch 91 to at least substantially close the open end. A wiping seal between cap 95 and the exterior of elongate body 53 is desirable to help clean body fluids and medications from the member 53 as it is withdrawn from a deployed position in a subject's throat.

Still with reference to FIG. 1, visible indicia 97 may be provided on an elongate member to assist in locating the nozzle 50 relative distal end 70 of tube 45. With reference now to FIG. 2, it is desirable to position nozzle 50 for discharge of atomized fluid, generally indicated at 99, exterior to conduit 68. Dispensing the misted fluid exterior the conduit enhances the probability that the medication will be dispensed in a dispersed form into the desired treatment area, and not condensed into drops in the tube 45. Indicia 97 and 85, in harmony, can even assist a therapist in deploying a distal end of nozzle 50 to a known position more distal than a distal opening of conduit 68.

Since the subject breathes through an installed endotracheal tube 45, it is generally desired to minimize any obstruction of the conduit 68 during medical procedures, such as application of atomized medications in pulmonary therapy. Therefore, nozzles 50 and elongate members 53 desirably are of relatively small diameter, compared to conduit 68. In the illustrated embodiment 40, nozzle 50 is about 0.2 inches in diameter, elongate member 53 is about 0.1 inches in diameter, and conduit 68 has an inside diameter of about 0.3 inches.

To assist in insertion and retraction of an atomizer assembly into and out of a tube 45, it is desirable for a cap 95 (if present) to provide a smooth sliding interface with elongate member 53. Furthermore, an elongate member will desirably provide sufficient stiffness to assist in sliding deployment of a nozzle in a distal direction. As an aide to such axial deployment, sometimes a stiffening member may be included in a body 53. One exemplary stiffening member is a wire which may be housed in a second conduit through elongate member 53. Such a wire may be malleable to assist in holding a deformed shape in elongate member 53.

Atomizer assembly 40 is adapted for medical use inside a subject, and as such, necessarily must be sterilizable. Therefore, all of the constituent components are manufactured from materials capable of sterilization. In general, components are made from medical grade polymers, including silicones, urethanes, and plastics. Typical materials of construction of a nozzle 50 include polycarbonate and other injection moldable plastics. Certain components of nozzles may also be made from silicone, or other materials. It is currently preferred to use medical grade tubing for the elongate member 53, although such is not a requirement. Elongate members 53 may be made from the same types of materials as used for nozzle assemblies.

A first type of atomizing nozzle assembly 110, suitable for use in the atomizer assembly 40, is illustrated in FIG. 3. Assembly 110 includes a nozzle body 112, and a resilient plug 115. Body 112 may be regarded as a thimble-shaped container, having a plug chamber 117 which contains plug 115. A distal end, generally indicated at 119, of body 112 has an exit orifice 122. An interior surface of end 119 provides structure defining a forward portion of a swirling chamber 125. Certain embodiments may also include a fluid ring 127.

Fluids are introduced into chamber 125 in a manner to promote revolution of the fluid prior to being expelled through orifice 122. The fluid therefore will have a transverse component of velocity when expelled axially through orifice 122. It is the tangential, or radial, velocity component, in combination with a change in pressure across the orifice 122, which causes the fluid to separate into small droplets as an atomized mist. Without such a tangential velocity component, developed in a swirling chamber 125, fluid will exit orifice 122 as a stream.

FIG. 3A illustrates an atomizer nozzle 112 with a plug 115 installed in an uncompressed position. FIG. 3B is a side view in section of the atomizer nozzle 112 illustrated in FIG. 3A, but with the plug 115 in a first compressed assembled position. FIG. 3C is a side view in section of the atomizer nozzle 112 illustrated in FIG. 3A, but with the plug in a second position further compressed by fluid flow.

The amount of compression to generate a bias in plug 115, in harmony with materials of composition of the nozzle assembly and elongate member, can set a minimum pressure threshold below which a fluid will not be dispensed through the nozzle assembly 110. A threshold pressure also helps assure that the dispensed fluid will be properly atomized. In one embodiment, a minimum pressure of about 5 pounds per square inch (psi) is required to initiate dispensing of a fluid. A threshold pressure ranging from essentially zero psi to close to the limit for pressure supplied by the pressurizable fluid source may be provided in a nozzle assembly. A typical arrangement connecting a nozzle assembly 110 to an elongate member 53 might compress a silicone plug 115 by 0.002 or 0.003 inches.

Illustrated plug 115 has a hexagonal cross-section, although such is not required for operation of an atomizing nozzle 110. Plug 115 simply should have a shape to cause fluid entering from conduit 140 to flow away from a nozzle centerline (or a centerline passing through the exit orifice 122), for subsequent redirection towards that centerline at the swirling chamber 125. Plug 115 may advantageously define a volume sized in harmony with a volume of plug chamber 117 to reduce the amount of fluid remaining in chamber 117 subsequent to operation of the nozzle 110.

As shown in FIG. 3, an elongate member 53 may include one or more conduits, such as conduits 140 and 142. As illustrated, conduit 140 is a fluid supply conduit to introduce fluids from a pressurized source into chamber 117. Pressurized fluid flows from a distal opening in conduit 140, through chamber 117, into swirling chamber 125, and exits the nozzle through orifice 122. Sometimes it is desirable to stiffen elongate member 53, or to enable defining a deformed shape in member 53. In such case, a malleable wire 143 may be disposed in a conduit 142. Wire 143 may function substantially to maintain a deformed shape in member 53, among other advantages.

Figure 4:
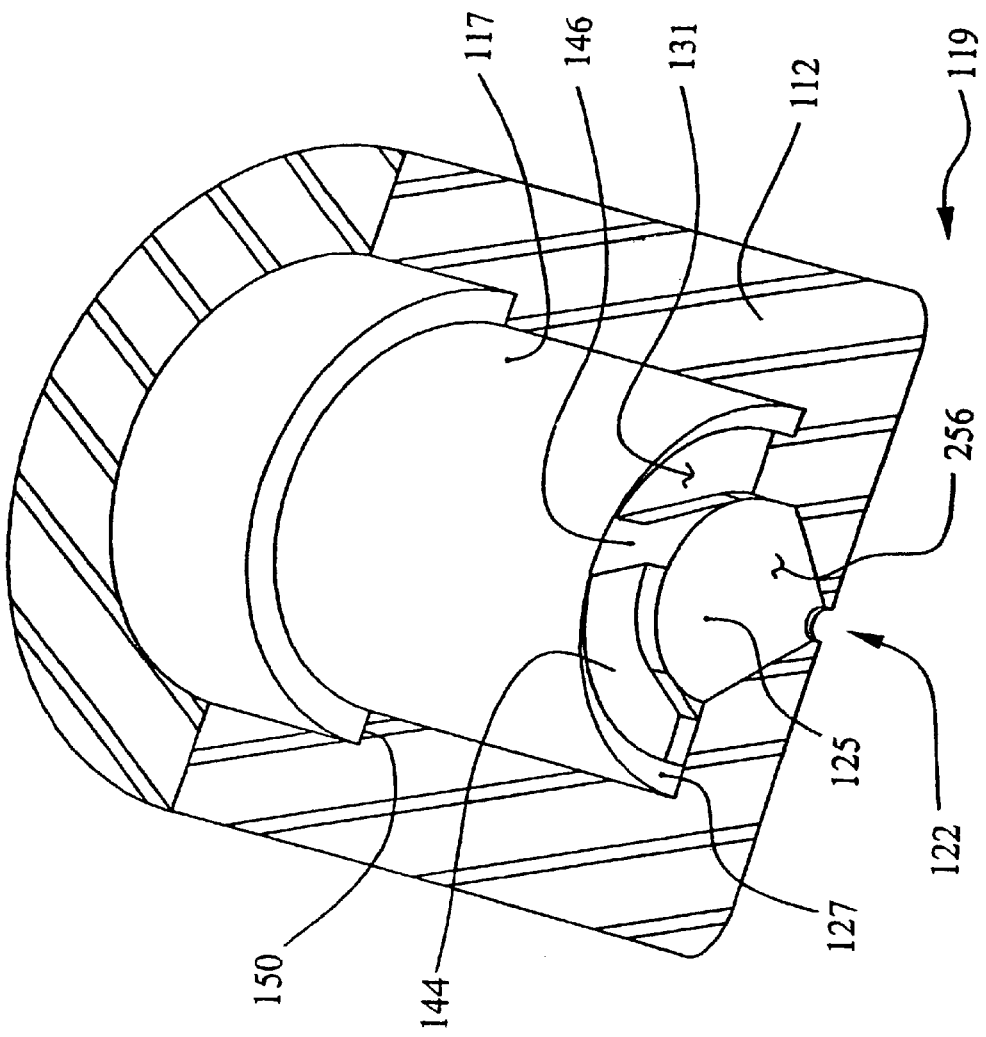
FIG. 4 is a rear view in perspective and in section of a portion of the nozzle body of the embodiment of FIG. 3.
Figure 5:
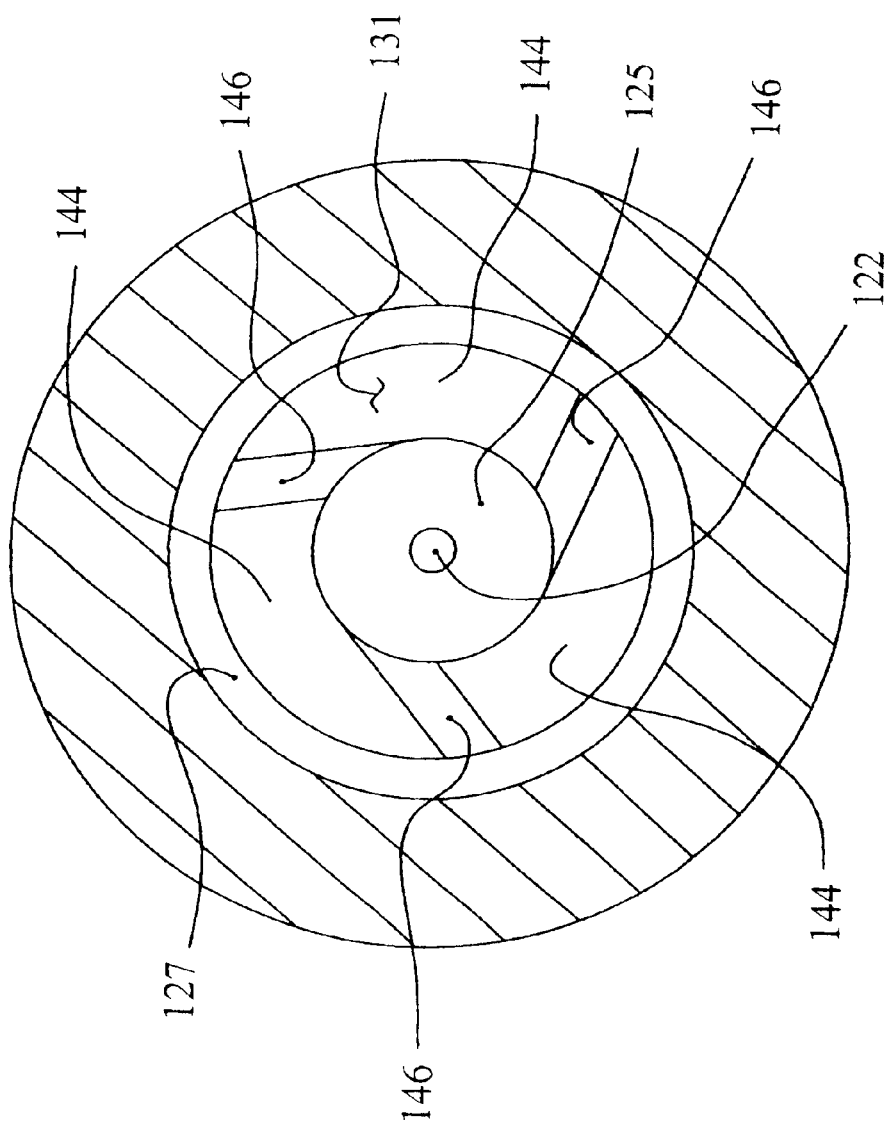
FIG. 5 is a rear view in section of an interior distal end of the embodiment of FIG. 3.

FIGS. 4 and 5 illustrate additional detail of certain structure which may be present in a valve body 112. As illustrated, a plurality of standoffs 144 may be arranged in sealing cooperation with a plug 115 to define a plurality of spaced apart turbine ports 146. FIG. 5 shows an embodiment having three standoffs 144 structured to form three turbine ports 146 spaced apart at about 120 degree intervals around an axis through exit orifice 122. Each of standoffs 144 can have a proximal surface 131 adapted sealingly to interface with the plug 115 to form the spaced apart fluid conduits, or turbine ports 146. Turbine ports 146 operate to direct fluid from a perimeter of chamber 117 into swirling chamber 125 for subsequent discharge through orifice 122.

A completely fluid-tight seal is not required between certain atomizer components, such as standoffs 144 and distal surface 135, so long as a sufficient quantity of fluid is directed through turbine ports 146 into swirling chamber 125 to enable the atomizing capability of a nozzle. A fluid ring 127 (if present) advantageously provides a similar fluid supply to each turbine port 146 to promote an equal flow through each such port. The rear portion of a swirling chamber 125 may be regarded as being provided, at least substantially, by that part of a distal surface 135 which is wetted by the therapeutic fluid.

A shoulder 150 may be provided (see, FIG. 4) as a stop defining an assembled position for a distal end 135 of elongate member 53. The shoulder 150 desirably is located in harmony with a length of plug 115 to provide the desired compression of a plug 115 between end 135 and standoff surfaces 131 on assembly of a body 112 to an elongate member 53. While many methods of manufacture are workable, it is presently preferred to attach a distal end 62 of an elongate member 53 to a proximal end of nozzle body 112 by a solvent bonding procedure. Other manufacturing methods including suitable adhesives, ultrasonic welding, and interference fits are within contemplation to attach a nozzle body 112 at a distal end 62 of an elongate member 53.

A second type of atomizing nozzle assembly, generally indicated at 210, adaptable for use in the atomizer assembly 40 (FIG. 1), is illustrated in FIGS. 6–11. Assembly 210 includes a nozzle body 212, carrying a post 215 internal to tip cavity 217 and adapted to interface with structure carried by tip member 220. Tip member 220 is structured to assemble into sealing relation with structure defining cavity 217. Similar to the first embodiment 110, cavity 218 in nozzle body 212 is structured for attachment at a distal end 62 of elongate member 53.

Figure 6:
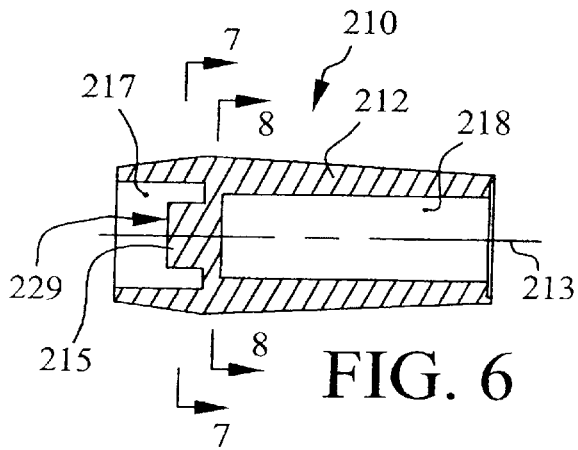
FIG. 6 is a side cross-section view in elevation of a body portion of a second atomizing nozzle.
Figure 7:
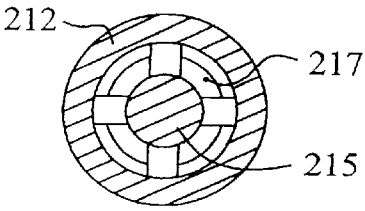
FIG. 7 is a view through section 7—7 of the embodiment of FIG. 6, and looking in the direction of the arrows.
Figure 9:
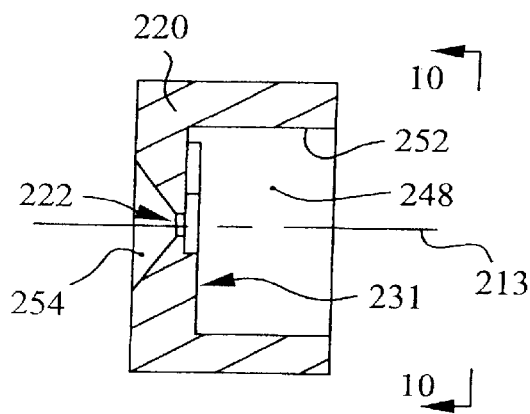
FIG. 9 is a side cross-section view in elevation of a tip portion of a second atomizing nozzle.
Figure 8:
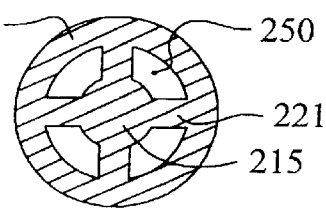
FIG. 8 is a view through section 8—8 of the embodiment of FIG. 6, and looking in the direction of the arrows.

A post 215 may be formed integral to a body 212, as best illustrated in FIGS. 6–8. As illustrated in FIG. 8, post 215 may be attached to a body 212 by one or more cantilevered brace elements 221. Alternatively, post 215 may be a separate component affixed to a body 212 to form a portion of a workable nozzle assembly 50. As a separate component, post may be attached by any workable method, non-exclusively including adhesives, solvent welding, ultrasonic welding, or an interference fit. Similar such methods may be used to attach a tip 220 to a body 212.

Post 215 functions similarly to plug 115 to distribute fluids (entering a nozzle assembly 50 from a supply conduit) in a direction away from centerline 213 passing through discharge orifice 222. Such distributed fluids may then be redirected radially towards centerline 213 and into swirling chamber 225 for subsequent discharge through exit orifice 222. Distal plug surface 229 typically is positioned during nozzle assembly to contact proximal standoff surface 231, thereby defining a rear surface for one or more turbine ports and a swirling chamber.

An interior surface of tip member 220 advantageously provides structure defining a forward portion of a swirling chamber 225. A rear portion of swirling chamber 225 can be defined by wetted portion of distal plug surface 229. Certain embodiments of tip member 220 may also include a fluid ring (not illustrated), similar to fluid ring 127 in the first nozzle embodiment. Also similar to the first embodiment 110, a plurality of standoffs 244 may be arranged in substantially sealing cooperation with post 215 to define a plurality of spaced apart turbine ports 246.

Figure 10:
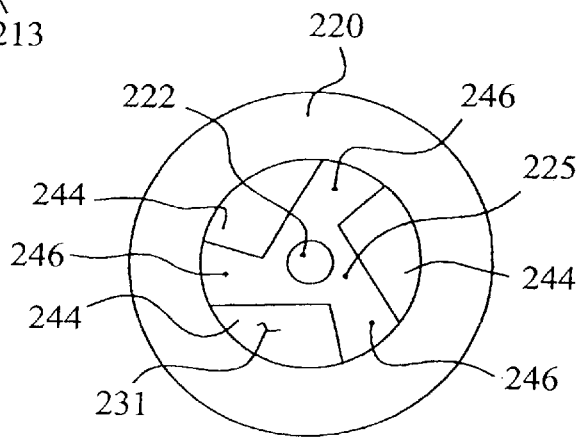
FIG. 10 is a rear view of the embodiment of FIG. 9, looking in the direction of arrows 10—10 in FIG. 9.
Figure 11:
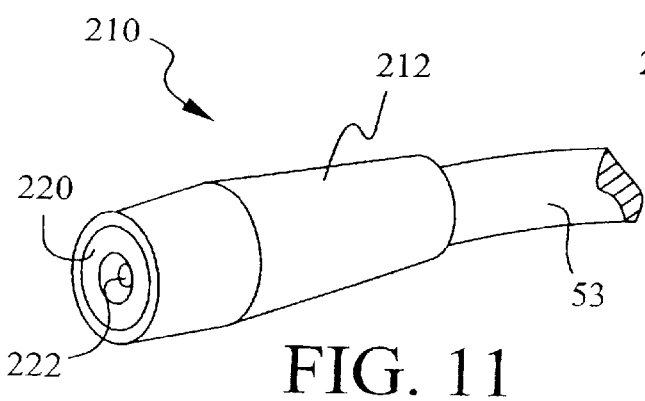
FIG. 11 is a front view in perspective of a second preferred atomizer nozzle assembly.

FIG. 10 illustrates an internal surface of forward end of second nozzle embodiment 210 having three standoffs 244 structured to form three turbine ports 246 spaced apart at about 120 degree intervals around axis 213 (FIG. 9) through exit orifice 222. One or more ports 246 can form a workable atomizing nozzle. An upper limit to the number of ports 246 is determined by manufacturing considerations. Each of standoffs 244 typically will have a proximal surface 231 adapted sealingly to interface with the plug 215 to form the spaced apart fluid turbine ports 246. Again, turbine ports 246 operate to direct fluid from a perimeter of tip cavity 217 into swirling chamber 225 for subsequent discharge through orifice 222. A fluid ring 127 (if present) advantageously provides a similar fluid supply to each turbine port 246 to promote an equal flow through each such port.

A post 215, similar to a plug 115, has a diameter smaller than an inside diameter of post cavity 248 to provide a fluid flow path through the nozzle. A nozzle 210 has a fluid flow path from chamber 218 to chamber 217, through ports 246, swirling chamber 225, and then continuing through exit orifice 222. As illustrated, fluid discharged from a supply conduit through elongate member 53, having a distal end 62 attached in chamber 218, passes through one or more passageways 250 (FIG. 8), then flows distally along the post 215 in post cavity 248. At a distal end of post 215, fluid is redirected through turbine ports 246 into swirling chamber 225. Ports 246 are configured to impart a spin to the fluid entering swirling chamber 225. Such spinning fluid has both axial and radial component of velocity when expelled through exit orifice 222.

A fluid steam having axial and radial components of velocity is atomized, or separated into small droplets, subsequent to a pressure drop across the exit orifice 222. The shape of the swirling chamber 225 can have an effect on the shape of the exiting atomized fluid cloud. The column of fluid passing through an exit orifice has a velocity profile with the fluid at the centerline having only an axial component of velocity, and fluid at the perimeter having the highest component of radial velocity. Higher radial velocity in a column of fluid generally corresponds to a larger diameter in the expelled atomized fluid cloud. A forcing cone 256 (FIG. 4) can promote increased spin in a column of fluid passing toward the exit orifice 122, resulting in a wider area of dispersal of the exiting mist. Particle size of the atomized fluid is also effected by the velocity profile in a discharge stream.

The axial length of an exit orifice 122, 222 has an effect on the shape of a discharged atomized fluid 99 cloud. As fluid passes along the length of the orifice, a boundary effect is imposed by the conduit walls between entry and exit planes defining the length of the passageway through the orifice 122, 222. Friction from the conduit wall reduces the velocity of the fluid, reducing the radial component of velocity. If the conduit were sufficiently long, the discharged fluid would exit as a stream. Therefore, the exit orifice is desirably made to have a short conduit length. One way to shorten such length without compromising structural integrity of a discharge tip is to form an exit cone 254 on the exterior surface of tip member 220. Alternatively, a cone 256 (FIG. 4) may be located on an internal surface.

It is within contemplation to make structural changes to the illustrated embodiments without changing their function. For example, post 215 may essentially be eliminated, with standoff surfaces 231 contacting a proximal end of chamber 217. In such a configuration, fluid would have its radially offset location from centerline 213 substantially defined by the configuration of port(s) 250. Furthermore, proximal skirt 252 may be eliminated, or disposed distally (substantially as a mirror image about a plane parallel to a distal end of body 212 in FIG. 9). A fluid ring 127 may be advantageous in such alternate embodiments to promote even fluid flow into turbine ports 246. Exit cone 254 may be eliminated by reducing the thickness of the forward portion of tip member 220. Alternatively, or additionally, a surface such as cone 254 may be relocated to, or added to, the internal surface to augment swirling chamber 225 in a modified second embodiment 210.

The nozzle assemblies described herein may be scaled to larger or smaller sizes. Bodies 112, 212 of currently preferred embodiments 110, 210, have bodies measuring about 0.2 inches in diameter for attachment to preferred elongate members 53 formed from medical grade tubing. The elongate member 53 typically has a first outside diameter, over which a body, having a second inside diameter, typically slides to form an attachment. The body has a third outside diameter being larger than the second diameter to form a wall having sufficient structural integrity to function in its intended use. It will be apparent to a skilled nozzle maker that if used with smaller diameter elongate members, nozzle assemblies as illustrated may be made considerably smaller in diameter. Such small diameter nozzle assemblies may be appropriate for insertion into small diameter conduits for delivery of therapeutic fluids as a mist. Such small diameter conduits non-exclusively may include catheters and various openings in a human body. The axially active one-way valve created by plug 115 may be scaled to a considerably smaller size than the radially active valve taught by the prior art, and which has a skirt sealing to a perimeter of a bore.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An atomizer assembly for delivery of fluids, substantially as a mist, to a pulmonary area of a subject, comprising:

an atomizing nozzle having a body with a diameter sized to fit within a first conduit through an endotracheal tube, and having a tip housing a swirling chamber in fluid communication with a discharge orifice;

an elongate tubular member comprising a second conduit for delivery of said fluids between a first end and a second end, said nozzle body being attached at said first end;

connection structure affixed at said second end of said tubular member, said connection structure being adapted to connect a pressurizable source of fluids into fluid communication with said second conduit; wherein:

said elongate member has a length, between said first and second ends, sufficient to enable extending said nozzle tip to a distal position inside said first conduit for discharge of fluids external to said endotracheal tube.

2. The atomizer assembly of claim 1, wherein:

said elongate member comprises a plurality of conduits between said first and second ends; and a malleable wire is disposed in one of said conduits and functions deformably to define a shape of said elongate member.

3. The atomizer assembly of claim 1, further comprising indicia visible on said elongate member and operable to indicate the relative position of said nozzle with respect to a distal end of a said endotracheal tube.

4. The atomizer assembly of claim 1, in combination with a branched adapter structured and arranged at a stem opening in said adapter for connection to a proximal end of said endotracheal tube, said elongate member being slidably extendable through a first branch opening in said adapter.

5. The atomizer assembly of claim 1, wherein:

said nozzle body comprises a thimble-shaped member having a distal interior end defining a forward portion of a swirling chamber having inlet ports and an exit orifice; a proximal end of said nozzle body being constructed and arranged for connection to said first end of said elongate member; and a rear portion of said chamber is defined by a distal end of a plug, said plug being deformable under an assembled self-bias such that a proximal end of said plug occludes an inlet at a distal end of said elongate member and thereby resists inadvertent discharge of a fluid therethrough, but wherein deliberate pressurization of said fluid causes said plug to deflect sufficiently to permit discharge of said fluid.

6. The atomizer assembly of claim 5, wherein said elongate member comprises medical grade tubing having a diameter of about ⅛ inches.

7. The atomizer assembly of claim 5, wherein:

said plug is received within a bore in said body;

said plug assumes a first deformed configuration during assembly to said elongate member; assumes a second deformed configuration when fluid is forced under pressure past said plug for discharge through said exit orifice; and returns to said first deformed configuration when pressure is sufficiently reduced on said fluid; and movement of said plug from said second to said first deformed configuration retracts fluid at said exit orifice back into the interior of said nozzle, whereby to help maintain a dry nozzle tip exterior.

8. The atomizer assembly of claim 1, wherein:

said nozzle comprises a tip element defining a forward portion of a swirling chamber having inlet ports and an exit orifice; and a post, affixed to body structure of said nozzle, is configured and arranged on assembly with said tip element to define a rear portion of said chamber.

9. The atomizer assembly of claim 8, a proximal end of said nozzle being constructed and arranged for connection to said elongate member comprising a medical grade tubing having a diameter of about 1/8 inches.

10. The atomizer assembly of claim 9, said nozzle consisting of a two piece assembly.

11. An atomizer comprising:
a body having a distal interior surface defining a forward portion of a swirling chamber having inlet ports and an exit orifice;
a plug housed within said body, said plug having a distal end defining a rear portion of said chamber; and
a fluid delivery conduit having a distal end with an entrance orifice disposed at a proximal end of said plug; wherein
said plug is resilient to deform and create a self-bias with said proximal plug end being configured and arranged to occlude said entrance orifice and resist inadvertent discharge of a fluid therethrough, but wherein deliberate pressurization of said fluid causes said plug to deflect sufficiently to permit discharge of said fluid through said entrance orifice.

12. The atomizer of claim 11, further comprising a fluid ring disposed upstream of said inlet ports to promote uniform fluid flow into said inlet ports.

13. The atomizer of claim 11, wherein:
said fluid delivery conduit is a passageway in an elongate tubular member;
said plug assumes a first deformed configuration during assembly of said body to said elongate member; assumes a second deformed configuration when fluid is forced under pressure past said plug for discharge through said exit orifice; and returns to said first deformed configuration when pressure is sufficiently reduced on said fluid; and
said plug and said chamber are sized in harmony such that movement of said plug from said second to said first deformed configuration retracts fluid at said exit orifice back into an interior of said body, thereby maintaining a dry nozzle tip.

14. The atomizer of claim 11, wherein the pressure required for discharge of a fluid is greater than about 5 psi.

15. The atomizer of claim 11, further comprising:
an elongate tubular member having proximal and distal ends with said fluid delivery conduit being disposed therebetween, a proximal end of said body being attached at said distal end of said elongate member; wherein
said self-bias of said plug is created by trapping said plug in compression between structure of said body and a forward end of said elongate member.

16. The atomizer of claim 15, wherein said elongate member comprises medical grade tubing having a diameter of about 1/8 inches.

17. The atomizer of claim 15, further comprising:
a plurality of conduits disposed between said first and second ends of said elongate member; and
a malleable wire disposed in one of said conduits and being functional to retain a deformable shape in said elongate member.

18. The atomizer of claim 15, in combination with an endotracheal tube having a first length between an open distal end and a proximal end, said elongate member in combination with said body having a second length such that said second length is longer than said first length.

19. The atomizer of claim 11, wherein:
said fluid delivery conduit is a passageway in an elongate tubular member;
said plug assumes a first deformed configuration during assembly of said body to said elongate member; assumes a second deformed configuration when fluid is forced under pressure past said plug for discharge through said exit orifice; and returns to said first deformed configuration when pressure is sufficiently reduced on said fluid; and
said plug and said chamber are sized in harmony such that movement of said plug from said second to said first deformed configuration promotes creation of a space between fluid remaining in said body and an exit plane of said exit orifice, thereby resisting tip dribble.

20. An atomizer comprising:
a tip member having a standoff and a surface defining a forward portion of a swirling chamber having turbine ports and an exit orifice;
a one-piece body forming a conduit for fluid communication between distal and proximal ends, said distal end including a post having a distal end surface configured to contact said standoff, a portion of said end surface defining a rear of said chamber; and
a fluid delivery conduit disposed at said proximal end of said body.

21. The atomizer of claim 20, further comprising a plurality of standoffs, said standoffs functioning to space apart a plurality of turbine ports.

22. The atomizer of claim 21, further comprising three standoffs spacing apart 3 turbine ports.

23. The atomizer of claim 21, said body being sized for reception within an endotracheal tube.

24. The atomizer of claim 23, further comprising an elongate member containing said fluid delivery conduit, and wherein a first end of said elongate member is attached at a proximal end of said body.

25. The atomizer of claim 24, wherein said elongate member comprises a plurality of conduits between first and second ends, and has a malleable wire disposed within one of said conduits, said wire being operable to maintain a deformed shape in said elongate member.

26. The atomizer of claim 26, wherein said elongate member has a length, between said first and second ends, of longer than about 14 inches.

27. The atomizer of claim 26, wherein said elongate member comprises medical grade tubing having a diameter of about 1/8 inch.

28. The atomizer of claim 27, in combination with a multibranch adapter having a stem adapted to fit to an endotracheal tube, said elongate member being slidingly disposed through a branch of said adapter.

29. The atomizer in combination of claim 28, further comprising a cap disposed at an opening of said branch housing said elongate member, said cap providing a wiping seal to a surface of said elongate member.

* * * * *